12) United States Patent
Hirota et al.

(10) Patent No.: US 7,074,947 B2
(45) Date of Patent: Jul. 11, 2006

(54) PROCESS FOR PRODUCING EPOXIDE COMPOUND

(75) Inventors: Masaji Hirota, Niihama (JP); Koji Hagiya, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 84 days.

(21) Appl. No.: 10/501,956

(22) PCT Filed: Jan. 31, 2003

(86) PCT No.: PCT/JP03/00956

§ 371 (c)(1),
(2), (4) Date: Jul. 21, 2004

(87) PCT Pub. No.: WO03/066615

PCT Pub. Date: Aug. 14, 2003

(65) Prior Publication Data

US 2005/0020841 A1    Jan. 27, 2005

(30) Foreign Application Priority Data

Feb. 8, 2002 (JP) .............................. 2002-032558

(51) Int. Cl.
*C07D 301/12* (2006.01)
*B01J 31/06* (2006.01)

(52) U.S. Cl. ...................... 549/531; 502/159; 502/160; 502/164

(58) Field of Classification Search ................. 549/531
See application file for complete search history.

(56) References Cited

U.S. PATENT DOCUMENTS

| 4,562,276 A | * | 12/1985 | Venturello et al. | ............. 556/20 |
| 4,595,671 A | * | 6/1986 | Venturello et al. | ........... 502/159 |
| 5,086,189 A | | 2/1992 | Lecloux et al. | |
| 5,274,140 A | * | 12/1993 | Venturello et al. | ........... 549/531 |
| 5,367,032 A | * | 11/1994 | Hancock et al. | ......... 525/333.8 |
| 5,780,655 A | | 7/1998 | Shum | |
| 6,054,407 A | | 4/2000 | Schulz et al. | |

FOREIGN PATENT DOCUMENTS

| JP | 3-236381 A | 10/1991 |
| JP | 11-349579 A | 12/1999 |
| JP | 2002-201147 A | 7/2002 |

* cited by examiner

*Primary Examiner*—Cecilia J. Tsang
*Assistant Examiner*—Raymond Covington
(74) *Attorney, Agent, or Firm*—Birch, Stewart, Kolasch & Birch, LLP

(57) ABSTRACT

A process for producing an epoxide compound, characterized by reacting an olefin compound with hydrogen peroxide in the presence of: a metal oxide catalyst obtained by reacting hydrogen peroxide with at least one member selected from the group consisting of tungsten metal, molybdenum metal, compounds of tungsten and a Group IIIb, IVb, Vb, or VIb element, tungstic acid and salts thereof, compounds of molybdenum and a Group IIIb, IVb, Vb, or VIb element, and molybodic acid and salts thereof; at least one member selected from the group consisting of tertiary amine compounds, tertiary amine oxide compounds, nitrogenous aromatic compounds, and nitrogenous aromatic N-oxide compounds; and a phosphoric acid compound.

5 Claims, No Drawings

PROCESS FOR PRODUCING EPOXIDE COMPOUND

TECHNICAL FIELD

The present invention relates to a process for producing an epoxide compound.

BACKGROUND ART

Epoxy compounds are very important compounds as various kinds of chemical products typically including resins, their synthetic intermediates, and the like. As their production processes, for example, oxidation of olefin compounds with peracids such as m-chloroperbenzoic acid, peracetic acid, etc. and organic peroxides such as tert-butyl hydroperoxide, etc. has been known. However, such a process uses a peracid or an organic peroxide which is relatively expensive, requires careful handling, and further requires troublesome post-treatment after completion of the reaction. Therefore, it has been desired to develop its production process without using peracids and organic peroxides.

On the other hand, recently, hydrogen peroxide has attracted attention as a clean and excellent oxidizing agent because it is cheap, is easy to handle and further comes out harmless water after completion of a reaction. Then, various processes for producing epoxy compounds by reacting olefin compounds with hydrogen peroxide have been reported. For example, JP 11-512335 W discloses an example of the production of cyclooctene oxide by reacting cyclooctene with hydrogen peroxide using a tungsten peroxo complex catalyst whose ligand is dimethyloctadecylamine oxide. However, since this process uses chloroform as a solvent which is problematic from the viewpoints of environment as well as working, safety and health. Therefore, it has been desired to develop a process for producing an epoxide compound from an olefin compound without using a solvent which is problematic from the viewpoints of environment as well as working, safety and health

DISCLOSURE OF THE INVENTION

Under these circumstances, the present inventors have studied a process for producing an epoxide compound from an olefin compound without using a solvent which is problematic from the viewpoints of environment as well as working, safety and health, intensively. As a result, the present inventors have found that an epoxide compound can be produced by reacting an olefin compound with hydrogen peroxide in the presence of a phosphoric acid compound in addition to a metal oxide catalyst obtained by reacting hydrogen peroxide with at least one member selected from the group consisting of tungsten metal, molybdenum metal, tungsten compounds composed of tungsten and a Group IIIb, IVb, Vb, or VIb element, tungstic acid and salts thereof, molybdenum compounds composed of molybdenum and a Group IIIb, IVb, Vb, or VIb element, and molybodic acid and salts thereof, and at least one member selected from the group consisting of tertiary amine compounds, tertiary amine oxide compounds, nitrogenous aromatic compounds, and nitrogenous aromatic N-oxide compounds, without using a solvent which is problematic from the viewpoints of environment as well as working, safety and health. Thus, the present invention has been accomplished.

That is, the present invention provides a process for producing an epoxide compound, which comprises reacting an olefin compound with hydrogen peroxide in the presence of:

a metal oxide catalyst obtained by reacting hydrogen peroxide with at least one member selected from the group consisting of tungsten metal, molybdenum metal, tungsten compounds composed of tungsten and a Group IIIb, IVb, Vb, or VIb element, tungstic acid and salts thereof, molybdenum compounds composed of molybdenum and a Group IIIb, IVb, Vb, or VIb element, and molybodic acid and salts thereof;

at least one member selected from the group consisting of tertiary amine compounds, tertiary amine oxide compounds, nitrogenous aromatic compounds, and nitrogenous aromatic N-oxide compounds; and a phosphoric acid compound.

EMBODIMENTS FOR CARRYING OUT THE INVENTION

First, the olefin compound to be used in the present invention will be illustrated.

The olefin compound to be used in the present invention is not specifically limited in so far as it has one of more olefinic carbon-carbon double bonds in its molecule. The two carbon atoms which form the double bond may be substituted with a hydrogen atom or atoms or substituent(s) such as a substituted or unsubstituted alkyl group or groups, a substituted or unsubstituted aryl group or groups, a substituted or unsubstituted aralkyl group or groups, a substituted or unsubstituted silyl group or groups, a halogen atom or atoms, or the like.

As the unsubstituted alkyl group, there is, for example, a C1–18 straight chain, branched chain, or cyclic alkyl group, and specific examples thereof include a methyl group, an ethyl group, an n-propyl group, an isopropyl group, an n-butyl group, an isobutyl group, a sec-butyl group, a tert-butyl group, an n-pentyl group, an n-hexyl group, an n-octyl group, an isooctyl group, an n-nonyl group, an n-decyl group, an adamantyl group, a cyclopentyl group, a cyclohexyl group, an undecyl group, a dodecyl group, a tridecyl group, a tetradecyl group, a pentadecyl group, a hexadecyl group, a heptadecyl group, an octadecyl. group, and the like.

Examples of the substituent of the substituted alkyl group include a C1–4 alkoxy group such as a methoxy group, an ethoxy group, an n-propoxy group, an isopropoxy group, an n-butoxy group, or the like, a silyl group such as a trimethylsilyl group, or the like, a halogen atom such as a fluorine atom, a chlorine atom, a bromine atom, or the like, etc.

As the unsubstituted aryl group, there are, for example, a phenyl group, a naphthyl group, and the like. Examples of the substituent of the substituted aryl group include the above alkyl group, alkoxy group, silyl group and halogen atom, and further a C2–3 acyl group such as an acetyl group, a propionyl group, and the like, etc. Specific examples of the substituted aryl group include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 2-methylphenyl group, a 4-methylphenyl group, a 4-methoxyphenyl group, a 4-acetylphenyl group, and the like.

As the substituted or unsubstituted aralkyl group, there is, for example, a group composed of the above substituted or unsubstituted alkyl group and the above substituted or unsubstituted aryl group, and specific examples thereof include a benzyl group, a phenylethyl group, a 4-fluorobenzyl group, 4-methoxybenzyl group, 2-chlorobenzyl group, and the like.

Examples of the silyl group include a silyl group substituted with groups selected from the above alkyl group and aryl group such as a trialkylsilyl group, and the like, for example, a trimethylsilyl group, a triethylsilyl group, a dimethylphenylsilyl group, a methyldiphenylsilyl group, and the like. Examples of the halogen atom include a fluorine atom, a chlorine atom, a bromine atom, and the like.

Further, the substituents of the carbon atoms which constitute the olefinic carbon-carbon double bond may be joined together to form a part of a ring structure, thereby forming a cyclic olefin compound, and specific examples of the ring include a cyclobutene ring, a cyclopentene ring, a cyclohexane ring, a cycloheptene ring, a norbornene ring, a cyclooctene ring, a cyclooctene ring, a cyclodecene ring, a cyclododecene ring, and the like. Of course, such a ring structure may be substituted with the above alkyl group, alkoxy group, silyl group, halogen atom, and the like. Specific examples of the olefin compound include monosubstituted olefins such as ethylene, propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl) styrene, allylbenzene, 4-methoxystyrene, safrole, eugenol, 3,4-dimethoxy-1-allylbenzene, and the like; disubstituted olefins such as 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methylcyclohexene, cycloheptene, cyclooctene, cyclodecene, cyclododecene, methylenecyclohexane, β-methylstyrene, stilbene, isosaflore, isoeugenol, β-pinene, norbornene, and the like; trisubstituted olefins such as 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)-cyclohexene, 1-isopropylcyclohexene, 2-carene, 3-carene, α-pinene, and the like; tetrasubstituted olefins such as 2,3-dimethyl-2-butene, 2,3,4-trimethyl-2-pentene, and the like; etc.

Among such olefin compounds, some of them exist as geometrical isomers and optical isomers. In the present invention, a single geometrical isomer or optical isomer may be used, or a mixture of geometrical isomers or a mixture of optical isomers may be used.

Then, the metal oxide obtained by reacting hydrogen peroxide with at least one member selected from the group consisting of tungsten metal, molybdenum, tungsten compounds composed of tungsten and a Group IIIb, IVb, Vb, or VIb element, tungstic acid and salts thereof, molybdenum compounds composed of molybdenum and a Group IIIb, IVb, Vb, or VIb element, and molybodic acid and salts thereof (hereinafter abbreviated as a metal compound) will be illustrated.

Examples of the tungsten compounds composed of tungsten and a Group IIIb element include tungsten boride, and the like; examples of the tungsten compounds composed of tungsten and a Group IVb element include tungsten carbide, tungsten silicide, and the like; examples of the tungsten compounds composed of tungsten and a Group Vb element include tungsten nitride, tungsten phosphide, and the like; and examples of the tungsten compounds composed of tungsten and a Group VIb element include tungstic oxide, tungstic acid, tungsten sulfide, and the like.

Examples of tungstic acid and salts thereof include tungstic acid and its salt with an alkali metal or an alkaline earth metal (e.g., sodium tungstate, etc.).

Examples of the molybdenum compounds composed of molybdenum and a Group IIIb element include molybdenum boride, and the like; examples of the molybdenum compounds composed of molybdenum and a Group IVb element include molybdenum carbide, silicide, and the like; examples of the molybdenum compounds composed of molybdenum and a Group Vb element include molybdenum nitride, molybdenum phosphide, and the like; and examples of the molybdenum compounds composed of molybdenum and a Group VIb element include molybdenum oxide, molybodic acid, molybdenum sulfide, and the like.

Examples of molybodic acid and salts thereof include molybodic acid and its salt with an alkali metal or an alkaline earth metal (e.g., sodium molybdate, etc.).

Among such metal compounds, tungsten metal, tungsten boride and molybdenum metal are preferred. Further, these metal compounds can be used alone or a mixture of two or more thereof. Furthermore, the metal compound having a finer particle size is preferably used from the viewpoint that the metal oxide which is a catalyst can be more readily prepared.

The metal oxide is prepared by reacting such a metal compound with hydrogen peroxide. As hydrogen peroxide, usually, an aqueous solution is used, while an organic solvent solution may be used. An aqueous solution of hydrogen peroxide is preferably used in view of easy handling. The concentration of hydrogen peroxide in an aqueous solution or an organic solvent solution is not specifically limited, but, practically, it is 1 to 60% by weight from the viewpoints of volumetric efficiency, safety and the like. As an aqueous solution of hydrogen peroxide, a commercially available one can be used as such or, if necessary, it can be used after adjusting the content of hydrogen peroxide by dilution, concentration, and the like. Further, an organic solvent solution of hydrogen peroxide can be prepared, for example, by means of extraction of an aqueous solution of hydrogen peroxide with an organic solvent, distillation in the presence of an organic solvent, or the like.

The amount of hydrogen peroxide to be used for preparation of the metal oxide is usually 3 mol or more, preferably 5 mol or more relative to 1 mol of the metal compound and there is no specific upper limit.

The reaction of the metal compound with hydrogen peroxide is usually carried out in an aqueous solution. Of course, it may be carried out in an organic solvent such as an ether solvent such as diethyl ether, methyl tert-butyl ether, tetrahydrofuran, etc., an ester solvent such as ethyl acetate, etc., a tertiary alcohol solvent such as tert-butanol, etc., a nitrile solvent such as acetonitrile, propionitrile, etc., or the like; or in a mixture of the organic solvent and water.

The temperature upon preparing the metal oxide is usually −10 to 100° C.

By reacting the metal compound with hydrogen peroxide in water or an organic solvent, all or a part of the metal compound is dissolved, thereby being able to prepare a uniform solution or suspension containing the metal oxide. The metal oxide may be isolated from such a liquid preparation by, for example, concentration, to use as the catalyst, or the liquid preparation as such can be used as the catalyst.

In order to improve the contact efficiency between the metal compound and hydrogen peroxide, preferably, the reaction is carried out with stirring so that the metal compound is thoroughly dispersed in the liquid preparation of the metal oxide. Further, in order to raise the contact efficiency between the metal compound and hydrogen peroxide, as well as to control the preparation of the metal oxide more easily, it is preferred to use the metal compound having a smaller particle size such as the metal compound in the form of powder, etc. Preferably, the liquid preparation of the metal oxide is adjusted to pH 2 to 3, if necessary, by addition of an alkali (e.g., an alkali metal hydroxide).

Next, the process for producing an epoxide compound by reacting the olefin compound and hydrogen peroxide in the presence of the metal oxide catalyst obtained in the above, and at least one member selected from the group consisting of tertiary amine compounds, tertiary amine oxide compounds, nitrogenous aromatic compounds, and nitrogenous aromatic N-oxide compounds. (hereinafter abbreviated as an amine compound) and a phosphoric acid compound will be illustrated.

As described above, the liquid preparation of the metal oxide may be used as the catalyst as such. Alternatively, the metal oxide may be isolated from the liquid preparation to use as the catalyst.

The amount of the metal oxide catalyst to be used is usually 0.001 to 0.95 mol, preferably 0.005 to 0.1 mole relative to 1 mol of the olefin compound.

Examples of the tertiary amine compound include trimethylamine, triethylamine, tri(n-propyl)amine, triisopropylamine, tri(n-butyl)amine, triisobutylamine, tri(n-pentyl)amine, tri(n-hexyl)amine, tri(n-heptyl)amine, tri(n-octyl)amine, tri(n-nonyl)amine, tri(n-decyl)amine, tri(n-dodecyl)amine, tri(n-tetradecyl)amine, tri(n-hexadecyl)amine, tri(n-octadecyl)amine, dimethylethylamine, dimethyl(n-propyl)amine, dimethylisopropylamine, dimethyl(n-butyl)amine, dimethylisobutylamine, dimethyl(n-pentyl)amine, dimethyl(n-hexyl)amine, dimethyl(n-heptyl)amine, dimethyl(n-octyl)amine, dimethyl(n-nonyl)amine, dimethyl(n-decyl)amine dimethy(n-undecyl)amine, dimethyl(n-dodecyl)amine, dimethyl(n-tetradecyl)amine, dimethyl(n-hexadecyl)amine, dimethyl(n-octadecyl)amine, methyldiethylamine, di(n-propyl)methylamine, diisopropylmethylamine, di(n-butyl)methylamine, diisobutylmethylamine, di(n-pentyl)methylamine, di(n-hexyl)methylamine, di(n-heptyl)methylamine, di(n-octyl)methylamine, di(n-nonyl)methylamine, di(n-decyl)methylamine, di(n-dodecyl)methylamine, di(n-tetradecyl)methylamine, di(n-hexadecyl)methylamine, di(n-octadecyl)methylamine, dimethylbenzylamine, di(n-butyl)benzylamine, di(n-hexyl)benzylamine, di(n-octyl)benzylamine, di(n-decyl)benzylamine, di(n-dodecyl)benzylamine, di(n-octadecyl)benzylamine, N,N-dimethylaniline, N,N-di(n-butyl)aniline, N,N-di(n-hexyl)aniline, N,N-di(n-octyl)aniline, N,N-di(n-decyl)aniline, N,N-di(n-dodecyl)aniline, N,N-di(n-octadecyl)aniline, N-methylmorpholine, N-(n-butyl)morpholine, N-(n-hexyl)morpholine, N-(n-octyl)morpholine, N-(n-decyl)morpholine, N-(n-dodecyl)morpholine, N-(n-hexadecyl)morpholine, N-(n-octadecylmorpholine), N-methylpyrrolidine, N-(n-butyl)pyrrolidine, N-(n-hexyl)pyrrolidine, N-(n-octyl)pyrrolidine, N-(n-decyl)pyrrolidine, N-(n-dodecyl)pyrrolidine, N-(n-hexadecyl)pyrrolidine, N-(n-octadecyl)pyrrolidine, N-methylpiperidine, N-(n-butyl)piperidine, N-(n-hexyl)piperidine, N-(n-octyl)piperidine, N-(n-decyl)piperidine, N-(n-dodecyl)piperidine, N-(n-hexadecyl)piperidine, N-(n-octadecyl)piperidine, and the like.

The tertiary amine oxide compound corresponds to the above tertiary amine compound wherein the nitrogen atom constituting its amino group is oxidized, and examples thereof include trimethylamine-N-oxide, triethylamine-N-oxide, N-methylmorphorine-N-oxide, and the like.

The nitrogenous aromatic compound corresponds to an aromatic compound wherein at least one of carbon atoms constituting the aromatic ring is replaced with a nitrogen atom, and examples thereof include pyridine compounds such as pyridine, 2-methylpyridine, 3-methylpyridine, 4-methylpyridine, 4-ethylpyridine, 4-(n-butyl)pyridine, 4-(1-hexyl)pyridine, 4-(1-hexyl)pyridine, 4-(1-octyl)pyridine, 4-(1-nonyl)pyridine, 4-(5-nonyl)pyridine, 4-(1-decyl)pyridine, 4-dimethylaminopyridine, 4-[di(n-hexyl)amino]pyridine, picolinic acid, pyridine-2,6-dicarboxylic acid, and the like. The nitrogenous aromatic N-oxide compound corresponds to the above nitrogenous aromatic compound wherein the nitrogen atom constituting the aromatic ring is oxidized, and examples thereof include pyridine-N-oxide compounds such as pyridine-N-oxide, and the like.

The amount of the amine compound to be used is usually 1 mol or more relative to 1 mol of the metal oxide, and there is no specific upper limit. However, since it is disadvantageous to use too much amount of the amine from the economical viewpoint, practically, the amount of the amine compound is 10 moles or less relative to 1 mol of the metal oxide.

The amine compound may be previously added to a reaction system upon preparation of the above metal oxide.

Examples of the phosphoric acid compound include phosphoric acid; alkali metal phosphates such as trisodium phosphate, tripotassium phosphate, disodium hydrogenphosphate, dipotassium hydrogenphosphate, sodium dihydrogenphosphate, potassium dihydrogenphosphate, etc.; alkaline earth metal phosphates such as calcium pyrophosphate, magnesium phosphate, etc.; and the like. Among these phosphoric acid compounds, when their hydrates are present, such hydrates may be used.

The amount of the phosphoric acid compound to be used is usually 0.1 to 10 moles, preferably 0.2 to 2 moles relative to 1 mol of the metal oxide.

The phosphoric acid compound may be previously added to a reaction system upon preparation of the above metal oxide.

Usually, hydrogen peroxide is used in the form of an aqueous solution, but its organic solvent solution may also be used. From the viewpoint of easy handling, to use an aqueous solution of hydrogen peroxide is preferred. The concentration of hydrogen peroxide in the aqueous solution or the organic solvent solution is not specifically limited but, practically, is 1 to 60% by weight in view of volumetric efficiency, safety, etc. As an aqueous hydrogen peroxide solution, a commercially available one may be used as such, or, if necessary, after adjusting: its content by dilution, concentration, etc. Further, the organic solvent solution of hydrogen peroxide can be prepared, for example, by means of extraction of an aqueous solution of hydrogen peroxide with an organic solvent, distillation in the presence of an organic solvent, or the like.

The amount of hydrogen peroxide to be used is usually 0.8 mol or more, preferably 1 mol of more relative to 1 mol of the olefin compound, and there is no specific upper limit. However, since it is disadvantageous to use too much amount of hydrogen peroxide from the economical viewpoint, practically, the amount of hydrogen peroxide is 5 moles or less, preferably 3 moles or less relative to 1 mol of the olefin compound.

The reaction of the olefin compound and hydrogen peroxide is carried out in the presence of the metal oxide, the amine compound and the phosphoric acid compound. This reaction may be carried out with no solvent, or in an aqueous solvent or in an organic solvent. Examples of the organic solvent include ether solvents such as diethyl ether, methyl tert-butyl ether, tetrahydrofuran, diglyme, etc.; ester solvents such as ethyl acetate, etc.; tertiary alcohol solvents such as tert-butanol, etc.; nitrile solvents such as acetonitrile, propionitrile, etc.; hydrocarbon solvents such as toluene, benzene, xylene, hexane, etc.; and the like. The amount of the solvent to be used is not specifically limited.

Usually, this reaction is carried out by contacting and mixing the metal oxide catalyst, the amine compound, the phosphoric acid compound, the olefin compound and hydrogen peroxide. For example, the metal compound, the amine compound, the phosphoric acid compound, the olefin compound and hydrogen peroxide are contacted and mixed to conduct the preparation of the metal oxide catalyst and the reaction of the olefin compound and hydrogen peroxide simultaneously.

The reaction temperature is usually −10 to 130° C. The reaction is usually carried out at atmospheric pressure, but it may also be carried out under reduced pressure or pressurized conditions.

As the reaction proceeds, an epoxide compound is produced. The progress of the reaction can be confirmed by a conventional analytic means such as gas chromatography, high performance liquid chromatography, thin layer chromatography, NMR, IR, and the like.

After completion of the reaction, the reaction mixture as such or, if necessary, after decomposing the remaining hydrogen peroxide with a reducing agent such as sodium sulfate, etc., is subjected to concentration, crystallization, etc. to isolate the desired epoxide compound. Further, the epoxide compound, can also be isolated by subjecting the reaction mixture, if necessary, after addition of water and/or a water-insoluble organic solvent thereto, to extraction. The epoxide compound thus isolated may be further purified by a conventional purification method such as distillation, column chromatography, recrystallization, and the like.

Examples of the epoxide compound thus obtained include ethylene oxide, propylene oxide, 1,2-epoxybutane, 1,2-epoxypentane, 4,4-dimethyl-1,2-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyoctadecane, 3,3-dimethyl-1,2-epoxybutane, cyclopentylethylene oxide, cyclohexylethylene oxide, 3-cyclohexyl-1,2-epoxypropane, styrene oxide, 4-(tert-butyl)styrene oxide, 3-phenyl-1,2-epoxypropane, 4-methoxystyrene oxide, safrole oxide, 3-(4-hydroxy-3-methoxyphenyl)-1,2-epoxypropane, 3-(3,4-dimethoxyphenyl)-1,2-epoxypropane, 2,3-epoxybutane, 2-methyl-1,2-epoxypropane, 2-methyl-1,2-epoxybutane, 2,3-epoxypentane, 2,3-epoxyhexane, 2-methyl-1,2-epoxyhexane,-3,4-epoxyhexane, 2,3-epoxyheptane, 3,4-epoxyheptane, 2,3-epoxyoctane, 3,4-epoxyoctane, 4,5-epoxyoctane, 2,3-epoxynonane, 2-methyl-1,2-epoxynonane, 3,4-epoxynonane,4,5-epoxynonane, 5,6-epoxydecane, 2-methyl-1,2-epoxyundecane, cyclopentene oxide, cyclohexene oxide, 4-methylcyclohexene oxide, cycloheptene oxide, cyclooctene oxide, cyclodecene oxide, cyclododecene oxide, β-methylstyrene oxide, stilbene, oxide, isosafrole oxide, 1-(4-hydroxy-3-methoxyphenyl)-1,2-epoxypropane, β-pinene oxide, norbornene oxide, 2-methyl-2,3-epoxybutane, 2-methyl-2,3-epoxypentane, 2-methyl-2,3-epoxyhexane, 2,5-dimethyl-2,3-epoxyhexa-4-ene, 2-methyl-2,3-epoxyheptane, 1-methyl-1,2-epoxycyclopentane, 1-methyl-1,2-epoxycyclohexane, 1-(tert-butyl)-1,2-epoxycyclohexane, 1-isopropyl-1,2-epoxycyclohexane, 2-carene oxide, 3-carene oxide, α-pinene oxide, 2,3-dimethyl-2,3-epoxybutane, 2,3,4-trimethyl-2,3-epoxypentane, and the like.

EXAMPLES

The following Examples further illustrate the present invention in detail, but are not to be construed to limit the scope of the present invention. The analysis was carried out by gas chromatography.

Example 1

A 100 mL-Schienk tube equipped with a reflux condenser was replaced with nitrogen, and 0.15 g of tungsten metal and 19.2 g of 30 wt % hydrogen peroxide were placed therein at room temperature. The mixture was stirred at the inner temperature of 50° C. for 15 minutes to obtain a liquid preparation of tungsten oxide. The liquid preparation was cooled to room temperature, to the liquid preparation was added 0.2 g of trisodium phosphate 12 hydrate and the mixture was stirred for 3 minutes. To this was added a solution of 4.4 g of cyclooctene and 0.42 g of tri(n-decyl) amine and the reaction was carried out by stirring and maintaining the mixture at the inner temperature of 60° C. for 3 hours. The resultant reaction mixture was cooled and separated into layers to obtain an organic layer containing cyclooctene oxide. The yield of cyclooctene oxide was 89% (on the basis of cyclooctene).

Example 2

An organic layer containing cyclooctene oxide was obtained according to the same manner as that described in Example 1, except that 0.16 g of tungsten boride was used instead of tungsten metal in Example 1. The yield of cyclooctene oxide was 88% (on the basis of cyclooctene).

Example 3

An organic layer containing cyclooctene oxide was obtained according to a similar manner as that described in Example 1, except that 0.16 g of tungsten carbide was used instead of tungsten metal in Example 1. The yield of cyclooctene oxide was 91% (on the basis of cyclooctene).

Example 4

A 100 mL-Schlenk tube equipped with a reflux condenser was replaced with nitrogen, and 0.15 g of tungsten metal and 19.2 g of 30 wt % hydrogen peroxide were placed therein at room temperature. The mixture was stirred at the inner temperature of 50° C. for 15 minutes to obtain a liquid preparation of tungsten oxide. The liquid preparation was cooled to room temperature, to the liquid preparation was added 0.2 g of trisodium phosphate 12 hydrate and the mixture was stirred for 3 minutes. To this was added a solution of 4.5 g of 1-octene and 0.42 g of tri(n-decyl)amine and the reaction was carried out by stirring and maintaining the mixture at the inner temperature of 60° C. for 4 hours. The resultant reaction mixture was cooled and separated into layers to obtain an organic layer containing 1,2-epoxyoctane. The yield of 1,2-epoxyoctane was 28% (on the basis of 1-octene).

Comparative Example 1

An organic layer containing 1,2-epoxyoctane was obtained according to a similar manner as that described in Example 4, except that 0.2 g of trisodium phosphate 12 hydrate in Example 4 was not used. The yield of 1,2-epoxyoctane was 8% (on the basis or 1-octene).

Example 5

A 100 mL-Schlenk tube equipped with a reflux condenser was replaced with nitrogen, and 0.26 g of sodium tungstate, 9.6 g of 30 wt % hydrogen peroxide and 0.32 g of phosphorus were placed therein at room temperature. The mixture was stirred at room temperature for 1 minute, and then adjusted to pH 2.3 with an aqueous sodium hydroxide solution to obtain a liquid preparation of tungsten oxide. To the liquid preparation was added a solution of 2.2 g of 1-octene, 0.42 g of tri(n-decyl)amine and 4 mL of toluene, and the reaction was carried out by stirring and maintaining the mixture at the inner temperature of 90° C. for 6 hours. The resultant reaction mixture was cooled and separated into layers to obtain an organic layer containing 1,2-epoxyoctane. The yield of 1,2-epoxyoctane is 41% (on the basis of 1-octene).

Comparative Example 2

An organic layer containing cyclooctene oxide was obtained according to a similar manner as that described in Example 7, except that 0.05 g of phosphoric acid in Example 5 was not used. The yield of cyclooctene oxide was 7% (on the basis of cyclooctene).

Example 6

A 100 mL-Schlenk tube equipped with a reflux condenser was replaced with nitrogen, and 0.074 g of molybdenum metal and 19.2 g of 30 wt % hydrogen peroxide were placed therein at room temperature. The mixture was stirred at room temperature for 2 minute to obtain a liquid preparation of molybdenum oxide. To the liquid preparation was added 0.05 g of phosphoric acid and the mixture was stirred for 3 minutes. To this was added a solution of 4.4 g of cyclooctene and 0.16 g of 4-(5-nonyl)pyridine, and the reaction was carried out by stirring and maintaining the mixture at the inner temperature of 60° C. for 2 hours. The resultant reaction mixture was cooled and separated into layers to obtain an organic layer containing cyclooctene oxide. The yield of cyclooctene oxide is 85% (on the basis of cyclooctene).

Comparative Example 3

The reaction was carried out according to a similar manner as that described in Example 6, except that 0.32 g of phosphoric acid in Example 6 was not used. No 1,2-epoxyoctane was obtained.

Example 7

A 100 mL-Schlenk tube equipped with a reflux condenser was replaced with nitrogen, and 0.15 g of tungsten metal and 19.2 g of 30 wt % hydrogen peroxide were placed therein at room temperature. The mixture was stirred at the inner temperature of 50° C. for 15 minutes to obtain a liquid preparation of tungsten oxide. The liquid preparation was cooled to room temperature, to the liquid preparation was added 0.05 g of phosphoric acid and the mixture was stirred for 3 minutes. To this was added a solution of 4.4 g of cyclooctene and 0.16 g of 4-(5-nonyl)pyridine and the reaction: was carried out by stirring and maintaining the mixture at the inner temperature of 60° C. for 2 hours. The resultant reaction mixture was cooled and separated into layers to obtain an organic layer containing cyclooctene oxide. The yield of cyclooctene oxide was 77% (on the basis of cyclooctene).

Comparative Example 4

An organic layer containing cyclooctene oxide was obtained according to a similar manner as that described in Example 7, except that 0.05 g of phosphoric acid in Example 7 was not used. The yield of cyclooctene oxide was 7% (on the basis of cyclooctene).

Example 8

A 100 mL-Schlenk tube equipped with a reflux condenser was replaced with nitrogen, and 0.074 g of molybdenum metal and 19.2 g of 30 wt % hydrogen peroxide were placed therein at room temperature. The mixture was stirred at room temperature for 2 minutes to obtain a liquid preparation of molybdenum oxide. To the liquid preparation was added 0.05 g of phosphoric acid and the mixture was stirred for 3 minutes. To this was added a solution of 4.4 g of cyclooctene and 0.16 g of 4-(5-nonyl)pyridine and the reaction was carried out by stirring and maintaining the mixture at the inner temperature of 60° C. for 2 hours. The resultant reaction mixture was cooled and separated into layers to obtain an organic layer containing cyclooctene oxide. The yield of cyclooctene oxide was 85% (on the basis of cyclooctene).

INDUSTRIAL APPLICABILITY

The process for producing an epoxide compound of the present invention is advantageous from the industrial viewpoint because the epoxide compound can be obtained by reacting an olefin compound and hydrogen peroxide in the presence of a readily available metal oxide obtained by reacting hydrogen peroxide with tungsten metal, a tungsten compound such as tungsten boride, etc., tungstic acid or a salt thereof, molybdenum metal, a molybdenum compound such as molybdenum boride, etc., or molybodic acid or a salt thereof, at least one member selected from the group consisting of tertiary amine compounds, tertiary amine oxide compounds, nitrogenous aromatic compounds, and nitrogenous aromatic N-oxide compounds, and a phosphoric compound, without using a solvent which is problematic from the viewpoints of environment as well as working, safety and health such as chloroform, etc.

The invention claimed is:

1. A process for producing an epoxide compound, which comprises reacting an olefin compound with hydrogen peroxide in the presence of:
   a metal oxide catalyst obtained by reacting hydrogen peroxide with at least one member selected from the group consisting of tungsten metal, molybdenum metal, tungsten compounds composed of tungsten and a Group IIIb, IVb, Vb, or VIb element, tungstic acid and salts thereof, molybdenum compounds composed of molybdenum and a Group IIIb, IVb, Vb, or VIb element, and molybodic acid and salts thereof;
   at least one member selected from the group consisting of tertiary amine compounds, tertiary amine oxide compounds, nitrogenous aromatic compounds, and nitrogenous aromatic N-oxide compounds; and a phosphoric acid compound.

2. The process for producing an epoxide compound according to claim 1, wherein the Group IIIb element is boron.

3. The process for producing an epoxide compound according to claim 1, wherein the Group IVb element is carbon.

4. The process for producing an epoxide compound according to claim 1, wherein the Group Vb element is phosphorus.

5. The process for producing an epoxide compound according to claim 1, wherein the Group VIb element is oxygen or sulfur.

* * * * *